(12) United States Patent  
Van Woezik

(10) Patent No.: US 6,968,040 B2
(45) Date of Patent: Nov. 22, 2005

(54) METHOD AND APPARATUS FOR IMPROVED X-RAY DEVICE IMAGE QUALITY

(75) Inventor: Johannes Theodorus Maria Van Woezik, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 58 days.

(21) Appl. No.: 10/175,987

(22) Filed: Jun. 20, 2002

(65) Prior Publication Data
US 2003/0095633 A1  May 22, 2003

(30) Foreign Application Priority Data
Nov. 20, 2001 (EP) .................................. 01202393

(51) Int. Cl.[7] .............................................. G21K 1/02
(52) U.S. Cl. ....................... 378/147; 378/156; 378/98.8
(58) Field of Search ........................... 378/7, 98.4, 146, 378/147, 145, 98.8, 156, 157, 158, 149, 108; 250/370.09; 382/132

(56) References Cited

U.S. PATENT DOCUMENTS

| | | | | |
|---|---|---|---|---|
| 4,761,802 A | * | 8/1988 | Kiri ........................... 378/98.4 |
| 4,773,087 A | * | 9/1988 | Plewes ........................ 378/146 |
| 4,896,344 A | * | 1/1990 | Grady et al. ................ 378/98.3 |
| 5,050,199 A | * | 9/1991 | Watanabe .................... 378/146 |
| 5,572,037 A | * | 11/1996 | Liu et al. .................. 250/483.1 |
| 5,666,396 A | * | 9/1997 | Linders et al. .............. 378/156 |
| 5,684,851 A | * | 11/1997 | Kurbatov et al. ............. 378/87 |
| 5,878,108 A | | 3/1999 | Baba et al. |
| 6,157,048 A | * | 12/2000 | Powell ........................ 257/59 |

\* cited by examiner

*Primary Examiner*—Edward J. Glick
*Assistant Examiner*—Irakli Kiknadze
(74) *Attorney, Agent, or Firm*—Douglas B. McKnight

(57) ABSTRACT

An X-ray device and method of improving the quality of an image formed by an X-ray device are provided. The X-ray device comprises a source emitting a beam of X-rays toward an object to be examined. A detector for receiving the X-rays that pass through the object is connected to an image processor. An X-ray collimator comprising a translatable element and at least one aperture for narrowing the beam of X-rays is arranged between the X-ray source and the examined object. A method of improving the quality of an image formed by the X-ray device comprises the steps of narrowing the X-ray beam using the aperture of the collimator, moving the aperture through the X-ray beam to expose the object to be examined to the narrowed X-ray beam, and forming an image of the examined object based upon the highest intensity value received for each pixel of the detector.

3 Claims, 3 Drawing Sheets

METHOD AND APPARATUS FOR IMPROVED X-RAY DEVICE IMAGE QUALITY

BACKGROUND

The present invention relates to an X-ray device for medical examination comprising an X-ray source emitting a beam of X-rays towards an object to be examined, an X-ray detector for receiving the X-rays passed through the object, image processing means, which are connected to the X-ray detector for forming an image of said object, X-ray collimator means, which are arranged between the X-ray source and the object for collimating the beam of X-rays. The invention also concerns a method of improving the image quality of such an X-ray device.

In all such X-ray devices known in the field the image quality suffers from the effects of scattered radiation. This scattered radiation arises when the primary or focal radiation interacts with low-density material. Usually the object is a human patient in which case water and bone are examples of low-density material. Scattered radiation has no specific direction and is detrimental for the resulting image. It causes "fog" in the image thereby reducing the image contrast.

An X-ray device and a method of improving the image quality thereof according to the preamble are described in U.S. Pat. No. 5,878,108. Herein the above-described problem is addressed by arranging an anti scatter grid behind the object and in front of the X-ray detector. Furthermore the recorded image is afterwards corrected for the effects of scattered radiation by means of mathematical image processing methods.

The known X-ray device and method of improving the image quality thereof have the disadvantage that the detected image information is disturbed by the fog and important image information is lost. The corrections made afterwards will furthermore inevitably introduce errors in the resulting image.

SUMMARY OF THE INVENTION

The object of the invention is to provide an X-ray device according to the preamble and a method of improving the image quality thereof by reducing the effects of scattered radiation in a different way.

Thereto the X-ray device according to the invention is characterized in that the X-ray collimator means comprise at least one area for narrowing the beam and means for moving the area through the beam for exposing the object to the narrowed beam and in that the image processing means are arranged to form the object image based on the highest intensity value received by the detector for each pixel.

The method of the invention aims at solving the above-described problem by the following steps:

a) narrowing the beam by means of at least one area formed by the X-ray collimator means;

b) moving the area through the beam for exposing the object to the narrowed beam; and c) forming the object image based on the highest intensity value received by the detector for each pixel.

By narrowing the beam the amount of scattered radiation reaching the detector is effectively reduced. The problem is thus addressed at the location where it arises. Since the area is movable through the beam it can thus cover the entire (part of the) object under examination. Advantageously only the information coming from primary X-rays is detected and processed, since the primary X-rays generally will have a higher intensity after passage through the object than the scattered X-rays. Consequently the image quality is considerably improved without the need for any complex mathematical corrections afterwards.

In a first preferred embodiment of the X-ray device the area is translatable through the beam. A translational movement of the area in synchronization with the overall control of the X-ray device can be realized fairly easily at relatively low cost.

In a practical embodiment of the X-ray device according to invention the area has a slit form. A slit form per se is widely known for collimating beams. Suitable objects with slits are available in all sizes and can also be easily manufactured for the intended use.

In a second preferred embodiment of the X-ray device the area is rotatable through the beam. A rotational movement of the area in synchronization with the overall control of the X-ray device can also be realized fairly easily at relatively low cost.

Preferably the rotatable area has a fan shape to ensure that the narrowed beam has effectively the same width over the entire length of the area in spite of the differences in speed of movement in radial direction. The rotational movement can elegantly be realized by means of an X-ray device, wherein the X-ray collimator means comprise a rotatable disc having an aperture.

The following description, claims and accompanying drawings set forth certain illustrative embodiments applying various principles of the present invention. It is to be appreciated that different embodiments applying principles of the invention may take form in various components, steps and arrangements of components and steps. These described embodiments being indicative of but a few of the various ways in which some or all of the principles of the invention may be employed in a method or apparatus. The drawings are only for the purpose of illustrating an embodiment of an apparatus and method applying principles of the present invention and are not to be construed as limiting the present invention.

BRIEF DESCRIPTION OF THE DRAWINGS

The foregoing and other features and advantages of the present invention will become apparent to those skilled in the art to which the present invention relates upon consideration of the following detailed description of apparatus applying aspects of the present invention with reference to the accompanying drawings, wherein.

DETAILED DESCRIPTION

Figure 1A:
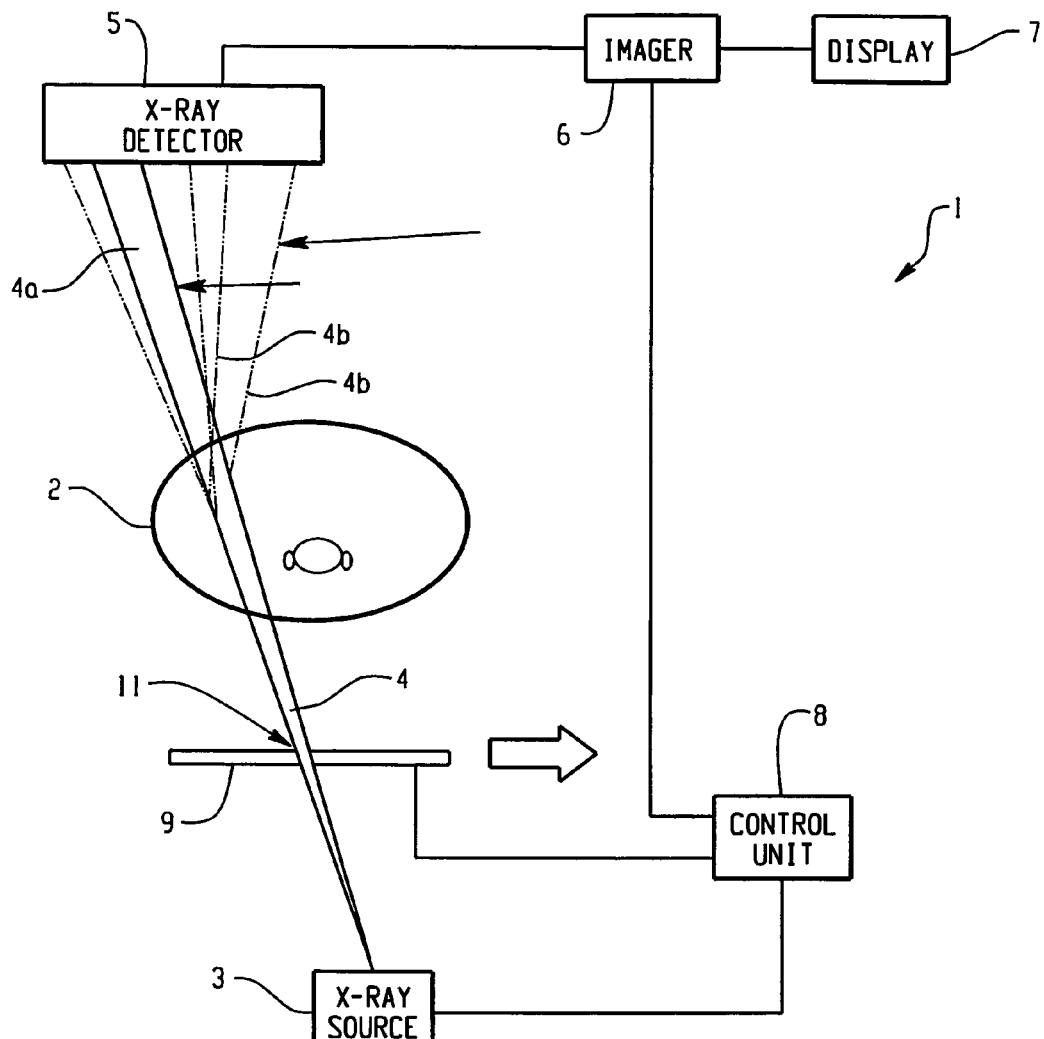
FIG. 1A schematically shows a first preferred embodiment of the X-ray device according to the invention.

In all figures equal elements are denoted with equal reference numerals. FIG. 1 schematically shows an X-ray device 1 for medical examination of an object 2, usually a human patient. X-ray device 1 comprises an X-ray source 3 for emitting a beam of X-rays 4 towards the object 2. An X-ray detector 5 is provided for receiving the X-rays 4 passed through the object. Due to local differences in the X-ray absorption within the object 2 an X-ray image is formed on an X-ray sensitive surface of the X-ray detector 5. Image processing means 6 are connected to the X-ray detector 5 for forming an electronic image of object 2 based on the X-ray image. The electronic image can be displayed, e.g. on a display screen 7 and/or stored for later use. Control means 8 synchronize the different components of X-ray device 1. X-ray devices of the type described are very well known in the field.

In the X-ray device 1 X-ray collimator means 9 are arranged between the X-ray source 3 and the object 2 for collimating the beam of X-rays 4. According to the invention the X-ray collimator means 9 comprise at least one area 11 for narrowing the beam 4. In the embodiment shown this area is formed by an aperture 11 in an element 9. Element 9 may have any shape, such as the plate-shape shown in FIG. 1.

Aperture 11 only allows part of the X-rays, denoted as 4, to pass. The X-rays 4 pass the object 2 and result in X-rays 4a forming the primary or focal beam and X-rays 4b forming the scattered beam. X-rays 4a comprise the relevant information about object 2, whereas X-rays 4b are needless and even detrimental to the resulting image. All X-rays are detected by the detector 5 and send to the image processing means 6. The image processing means are arranged to form the object image based on the highest intensity value received by the detector for each pixel. Preferably this is realized by comparing each new intensity value for each pixel with the already stored earlier value for that pixel and storing the new value only when it is higher than the earlier value. Detectors that are capable of this are already known in the field and are referred to as "top detectors", for example in electronic circuitry or in a software environment.

Figure 1B:
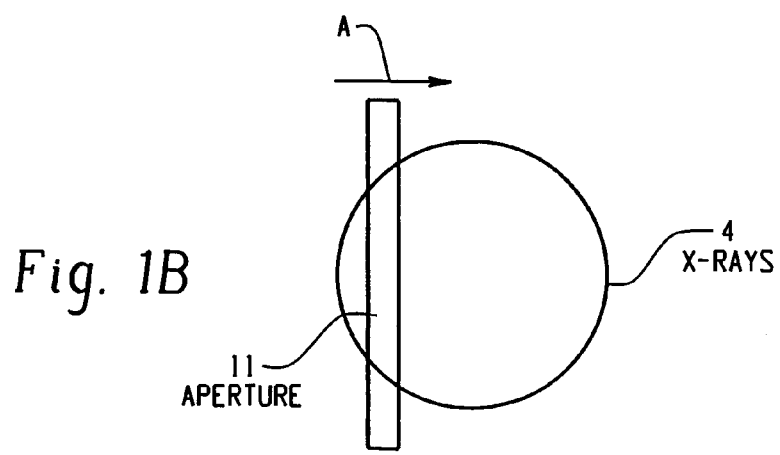
FIG. 1B schematically illustrates the functioning of the X-ray collimator means of the first preferred embodiment.

FIG. 1B schematically illustrates the functioning of the X-ray collimator means 9. Plate-shaped element 9 with aperture 11 is movable through the beam 4. In the embodiment shown the movement is a translation, which for ease of explanation only follows the direction of arrow A. It will be apparent to a person skilled in the art that the translation can take place in all directions provided that the direction is matched to the shape and/or orientation of the detector.

The plate-shaped collimator means 9 are preferably constructed of a material that effectively blocks all X-rays. The only X-rays reaching the object 2 are those X-rays that pass the aperture 11. By moving the aperture 11 through the beam the object 2 (or the relevant part thereof) is subjected piece by piece to the X-rays. Thus effectively a narrow beam is formed to dynamically scan the object.

The movement of the collimator means 9 takes place under the control of control means 8. Many ways of realizing this movement will appear to a person skilled in the art. Aperture 11 in this case has a slit-form. However, other suitable forms can be used, such a rectangle or a even a circle, provided that the control means are arranged to cover essentially the entire cross section of the beam with the aperture.

It is noted that in case an anti scatter grid is mounted in front of the X-ray detector the direction of the aperture preferably is perpendicular to the lines of the grid.

Figure 2A:
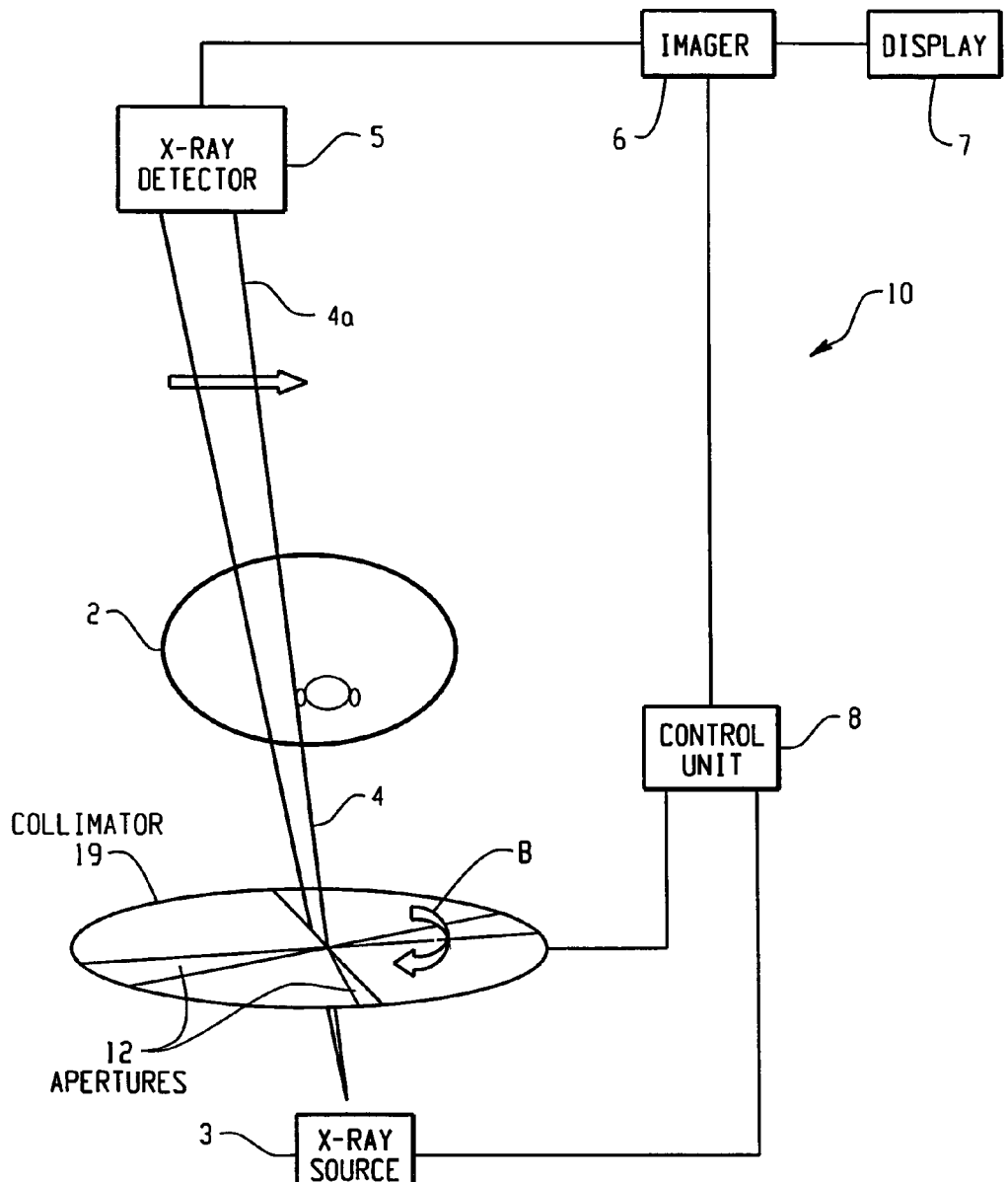
FIG. 2A schematically shows a second preferred embodiment of the X-ray device according to the invention.

FIG. 2A schematically shows a second preferred embodiment 10 of the X-ray device according to the invention. X-ray device 10 differs from X-ray device 1 with respect to the embodiment of the X-ray collimator means, which comprise a rotatable disc 19 having a number of apertures 12.

Figure 2B:
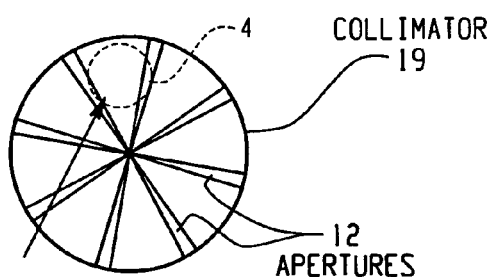
FIG. 2B schematically illustrates the functioning of the X-ray collimator means of the second preferred embodiment.

FIG. 2B schematically illustrates the functioning of these X-ray collimator means 19.

Disc 19 rotates, for instance in the direction of arrow B or the other way around, through the beam 4. The movement of disc 19 takes place under the control of control means 8. Many ways of realizing this movement will appear to a person skilled in the art.

Apertures 12 in this case have a fan shape. However, other suitable shapes can be used, such as a slit shape or a rectangular shape or even a circle. The number of apertures may vary. In another embodiment the disc may have one aperture extending across the diameter of the disc. Preferably the diameter of the disc is then approximately twice the size of the diameter of the beam. Preferably the control means are arranged to cover essentially the entire cross section of the beam with the aperture(s).

The disc 19 is preferably constructed of a material that effectively blocks all X-rays. The only X-rays reaching the object 2 are those X-rays that pass the apertures 12. By moving the apertures 12 through the beam the object 2 (or the relevant part thereof) is subjected piece by piece to the X-rays. Thus again effectively a narrow beam is formed to dynamically scan the object.

In general preferably the area has a width of essentially 5 centimeter, when measured at the entrance of the detector. Given a desirable exposure time of 200 milliseconds this leads to a speed of movement of 25 centimeter per second yielding a recording time of approximately 1 second for a nine inch image intensifier. It is noted that the desirable exposure time depends on the x-ray sensitivity of the image detector and on the intensity of the primary beam.

Figure 3:
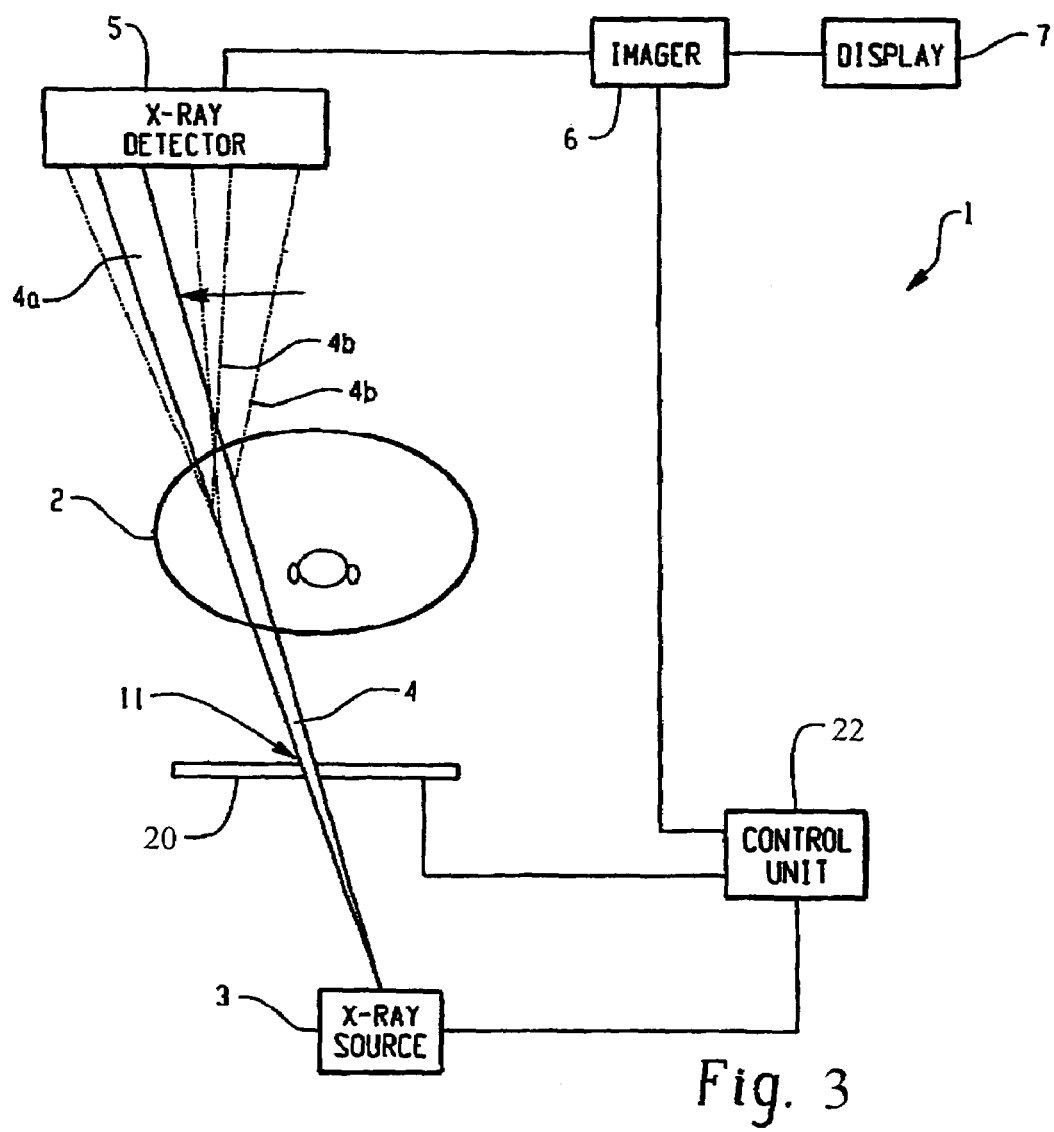
FIG. 3 schematically shows an alternate embodiment of the X-ray device in which like elements with FIG. 1A are labeled with like reference numbers.

With reference to FIG. 3, alternatively the X-ray collimator means can be formed by means of a so-called 'Dynamic Beam Attenuator' (DBA) 20. In short this DBA is an X-ray filter comprising a matrix of capillary tubes, that are filled with an X-ray absorbing fluid. The level of X-ray absorbing fluid inside the capillary tubes determines the measure of absorption of X-rays by that tube. This level is controllable by a control 22 means which applies an electric force to a number of selected capillary tubes. The DBA is described in more detail in U.S. Pat. No. 5,666,396 by the same applicant, which is incorporated herein by reference.

Since each capillary tube or each group of capillary tubes is separately controllable a person skilled in the art will be able to form at least one area in the DBA for narrowing the beam and for moving the area through the beam for exposing the object to the narrowed beam. The DBA may then function as an X-ray collimator, when the area is transparent to X-rays like an aperture in a mechanical element. Alternatively the DBA may function as a combined X-ray collimator/filter in which the area filters the passing X-rays. Additional filter elements, which will have to be used in combination with the earlier described embodiments, are now redundant.

It is noted that the invention reveals the use of an X-ray device as described for improving the image quality thereof by performing the following steps:

a) narrowing the beam by means of at least one area formed by the X-ray collimator means;

b) moving the area through the beam for exposing the object to the narrowed beam; and c) forming the object image based on the highest intensity value received by the detector for each pixel.

The invention is of course not limited to the described or shown embodiments, but generally extends to any embodiment, which falls within the scope of the appended claims as seen in light of the foregoing description and drawings. While a particular feature of the invention may have been described above with respect to only one of the illustrated embodiments, such features may be combined with one or more other features of other embodiments, as may be desired and advantageous for any given particular application. From the above description of the invention, those skilled in the art will perceive improvements, changes and modification. Such improvements, changes and modification within the skill of the art are intended to be covered by the appended claims.

Having described a preferred embodiment of the invention, the following is claimed:

1. An X-ray device comprising:
   an X-ray source for emitting a beam of X-rays towards an associated object to be examined;
   an X-ray detector having a plurality of pixels sized for receiving the beam of X-rays passed through the object;
   means for image processing connected to the X-ray detector for forming an image of said object;
   means for collimating X-rays between the X-ray source and the object, such that only a fraction of the beam reaches the object and the detector and such that some pixels of the detector detect radiation that has passed directly from the source through the object to the detector and other pixels receive only scattered radiation, the means for collimating X-rays comprising at least one area having a fan shape for narrowing the beam; and
   means for rotating the at least one area through the beam for exposing the object to the narrowed beam such that the detector pixels that detect radiation directly from the source and the pixels that receive only scattered radiation change as the at least one area rotates wherein the means for image processing forms the object image based on the highest intensity value received by the detector for each pixel during the rotation of the at least one area.

2. The X-ray device of claim 1 wherein the means for collimating X-rays comprise a rotatable disc having a plurality of fan-shaped apertures.

3. A method of improving the image quality of an X-ray device, the method comprising the steps of:
   emitting a beam of X-rays towards an object to be examined;
   collimating the emitted beam of x-rays with at least one fan-shaped aperture formed in a collimator to form a narrowed beam with a fan-shaped cross-section;
   moving the fan-shaped aperture through the beam for exposing successive portions of the object to the narrowed beam of fan-shaped cross-section as the aperture moves;
   as the fan-shaped aperture moves, sweeping the narrowed beam across pixels of a detector, some of the pixels receiving radiation that has passed directly through the aperture and object to the detector and others detect only scattered radiation, the pixels receiving the direct and scattered only changing as the aperture moves;
   repeated sampling the pixels such that each pixel has higher intensity values when receiving radiation directly through the aperture and the object and each pixel has lower intensity values when receiving only scattered radiation;
   processing images of said object from the detected received X-rays wherein the step of processing images includes forming the object image based on the highest intensity value received by the detector for each pixel.

* * * * *